(12) United States Patent
Zhang et al.

(10) Patent No.: US 11,534,063 B2
(45) Date of Patent: Dec. 27, 2022

(54) INTERPUPILLARY DISTANCE MEASURING METHOD, WEARABLE OPHTHALMIC DEVICE AND STORAGE MEDIUM

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Hao Zhang, Beijing (CN); Lili Chen, Beijing (CN); Minglei Chu, Beijing (CN); Jiankang Sun, Beijing (CN); Guixin Yan, Beijing (CN); Ziqiang Guo, Beijing (CN); Yakun Wang, Beijing (CN); Wenhong Tian, Beijing (CN); Zhanshan Ma, Beijing (CN)

(73) Assignees: BEIJING BOE OPTOELECTRONICS TECHNOLOGY CO., LTD., Beijing (CN); Beijing BOE Technology Development Co., Ltd., Beijing (CN)

( * ) Notice: Subject to any disclaimer, the term of this patent is extended or adjusted under 35 U.S.C. 154(b) by 1036 days.

(21) Appl. No.: 16/096,428

(22) PCT Filed: Feb. 1, 2018

(86) PCT No.: PCT/CN2018/074980
§ 371 (c)(1),
(2) Date: Oct. 25, 2018

(87) PCT Pub. No.: WO2019/007050
PCT Pub. Date: Jan. 10, 2019

(65) Prior Publication Data
US 2021/0228075 A1    Jul. 29, 2021

(30) Foreign Application Priority Data

Jul. 7, 2017  (CN) .......................... 201710551489.5

(51) Int. Cl.
*A61B 3/11* (2006.01)
*G06T 7/73* (2017.01)
*A61B 3/00* (2006.01)

(52) U.S. Cl.
CPC ............ *A61B 3/111* (2013.01); *A61B 3/0025* (2013.01); *G06T 7/73* (2017.01); *G06T 2207/10048* (2013.01); *G06T 2207/30041* (2013.01)

(58) Field of Classification Search
CPC ......... A61B 3/111; A61B 3/0025; G06T 7/73; G06T 2207/10048; G06T 2207/30041;
(Continued)

(56) References Cited

U.S. PATENT DOCUMENTS

| 9,538,166 B2 | 1/2017 | Yu et al. |
| 2005/0068495 A1* | 3/2005 | Jojiki ...................... A61B 3/111 351/204 |

(Continued)

FOREIGN PATENT DOCUMENTS

| CN | 103793719 A | * | 5/2014 |
| CN | 103793719 A | | 5/2014 |

(Continued)

OTHER PUBLICATIONS

International Search Report of PCT/CN2018/074980 in Chinese, dated Apr. 20, 2018 with English translation.
(Continued)

*Primary Examiner* — Mohammed A Hasan
(74) *Attorney, Agent, or Firm* — Collard & Roe, P.C.

(57) ABSTRACT

An interpupillary distance measuring method, a wearable ophthalmic device and a computer readable storage medium are provided. The method includes: capturing at least one eye image; extracting corresponding one or two pupil image positions corresponding to a monocular pupil or pupils to
(Continued)

two eyes in the at least one eye image; and determining an actual distance between the pupils of two eyes according to the one or two pupil image positions.

9 Claims, 10 Drawing Sheets

(58) Field of Classification Search
CPC . G06T 2207/30201; G06T 7/62; G06T 5/002; G06T 7/10; H04N 5/232
USPC .......................................................... 351/204
See application file for complete search history.

(56) References Cited

U.S. PATENT DOCUMENTS

| | | | | |
|---|---|---|---|---|
| 2008/0049185 | A1* | 2/2008 | Huffman | A61B 3/113 351/206 |
| 2015/0055086 | A1* | 2/2015 | Fonte | G02C 13/001 351/178 |
| 2016/0041048 | A1 | 2/2016 | Blum et al. | |
| 2017/0112378 | A1* | 4/2017 | Tamkin | A61B 3/154 |

FOREIGN PATENT DOCUMENTS

| | | | |
|---|---|---|---|
| CN | 104834381 | A | 8/2015 |
| CN | 106019588 | A | 10/2016 |
| CN | 106325510 | A | 1/2017 |
| CN | 106686365 | A | 5/2017 |
| CN | 106803950 | A * | 6/2017 |
| CN | 106803950 | A | 6/2017 |
| JP | S53106070 | A | 9/1978 |
| JP | 2003028614 | A | 1/2003 |
| JP | 2012239566 | A | 12/2012 |
| JP | 2015001432 | A | 1/2015 |

OTHER PUBLICATIONS

Notice of Transmittal of the International Search Report of PCT/CN2018/074980 in Chinese, dated Apr. 20, 2018.
Written Opinion of the International Searching Authority of PCT/CN2018/074980 in Chinese, dated Apr. 20, 2018 with English translation.
Extended European Search Report in European Application No. 18788993.6 dated Feb. 23, 2021 in English.
Zhang et al., Gaze Estimation in a Gaze Tracking System, Science China Information Sciences, Research Papers, Nov. 2011, pp. 2295-2306; vol. 54, No. 11.
Chinese Office Action in Chinese Application No. 201710551489.5, dated Aug. 2, 2019 with English translation.
Japanese Office Action in Japanese Application No. 2018-557090 dated Dec. 20, 2021.
Japanese Office Action in Japanese Application No. 2018-557090 dated Jul. 13, 2022.

* cited by examiner

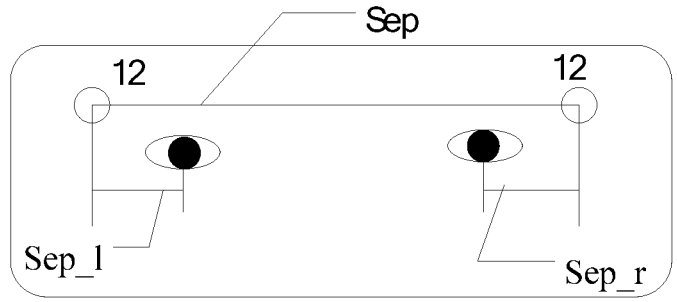

Capturing an eye image including the monocular pupil and a set marker
401

Extracting the pupil image position of the monocular pupil in the eye image, and extracting the mark position of the marker from the eye image
411

Determining the horizontal image distance between the monocular pupil and the marker according to the pupil image position of the monocular pupil and the mark position
421

Determining the actual distance between the pupils of two eyes according to the horizontal image distance between the monocular pupil and the mark position
431

Extracting an image area provided with one eye or two eyes from respective eye image
501

Obtaining a grayscale image by filtering and graying of the image area, and converting the grayscale image into a binary image
511

Finding the boundary of the monocular pupil area or the boundary of the binocular pupil area in the binary image
521

Obtaining one or two elliptical graphics by ellipse fitting of the boundary of the monocular pupil area or the boundary of the binocular pupil area
531

Taking the center of each elliptical graphic as the image position of corresponding pupil
541

FIG. 5

Wearable ophthalmic device
600

Infrared Source 604

Camera 601

Memory 603

Processor 602

FIG. 6

INTERPUPILLARY DISTANCE MEASURING METHOD, WEARABLE OPHTHALMIC DEVICE AND STORAGE MEDIUM

CROSS REFERENCE TO RELATED APPLICATIONS

This application is the National Stage of PCT/CN2018/074980 filed on Feb. 1, 2018, which claims priority under 35 U.S.C. § 119 of Chinese Application No. 201710551489.5 filed on Jul. 7, 2017, the disclosure of which is incorporated by reference.

TECHNICAL FIELD

Embodiments of the disclosure relates to an interpupillary distance measuring method, a wearable ophthalmic device and a storage medium.

BACKGROUND

With the continuous development of virtual reality (VR) technology, people have higher and higher requirement on VR devices. For example, VR devices are required to have a higher refresh rate to reduce trailing smear, and screens are required to have higher resolution to reduce visual graininess. In addition, people's requirements for anti-distortion and anti-dispersion of VR devices are getting higher and higher. If the anti-distortion anti-dispersion operation does not consider the difference of the pupils of the human eyes, different viewing effects will be caused when the same VR device is used by people with different interpupillary distances.

SUMMARY

At least one embodiment of the disclosure provides an interpupillary distance measuring method, comprising: capturing at least one eye image; from the at least one eye image, extracting one pupil image position corresponding to a monocular pupil, or extracting two pupil image positions corresponding to pupils of two eyes; and determining an actual distance between the pupils of two eyes according to the one or two pupil image positions.

For example, capturing the at least one eye image includes: capturing an eye image simultaneously including the pupils of two eyes; extracting the two pupil image positions corresponding to the pupils of two eyes in the at least one eye image includes: determining the pupil image positions of the pupils of two eyes in the eye image; and determining the actual distance between the pupils according to the one or two pupil image positions includes: determining an image distance of the pupils of two eyes on the eye image according to the pupil image positions of the pupils of two eyes; and determining the actual distance between the pupils of two eyes according to the image distance of the pupils of two eyes.

For example, determining the actual distance between the pupils of two eyes according to the image distance of the pupils of two eyes includes: measuring a vertical actual distance between the two eyes and a camera; determining a field of view (FOV) of the camera; reading the image distance of the pupils of two eyes; reading a height of the eye image; and determining the actual distance between the pupils of two eyes according to the image distance of the pupils of two eyes, the FOV, the vertical actual distance between the two eyes and the camera, and the height of the eye image.

For example, capturing the at least one eye image includes: adopting a first camera and a second camera to respectively capture a left-eye image including a left eye and a right-eye image including a right eye; extracting the one pupil image position corresponding to the monocular pupil in the at least one eye image, from the at least one eye image, includes: determining the pupil image position of the left-eye pupil in the left-eye image and the pupil image position of the right-eye pupil in the right-eye image; and determining the actual distance between the pupils of two eyes according to the one or two pupil image positions includes: determining an image position of the first camera in the left-eye image and an image position of the second camera in the right-eye image; determining a first horizontal image distance between the pupil image position of the left-eye pupil and the image position of the first camera in the left-eye image; determining a first horizontal actual distance between the left-eye pupil and the first camera according to the first horizontal image distance; determining a second horizontal image distance between the pupil image position of the right-eye pupil and the image position of the second camera in the right-eye image; determining a second horizontal actual distance between the right-eye pupil and the second camera according to the second horizontal image distance; and determining the actual distance between the pupils of two eyes according to the first horizontal actual distance and the second horizontal actual distance.

For example, determining the first horizontal actual distance between the left-eye pupil and the first camera according to the first horizontal image distance includes: measuring a vertical actual distance between the first camera and the second camera and the two eyes; determining a first FOV of the first camera; reading a height of the left-eye image; and determining the first horizontal actual distance between the left-eye pupil and the first camera according to the vertical actual distance, the first FOV, the first horizontal image distance, and the height of the left-eye image; and determining the second horizontal actual distance between the right-eye pupil and the second camera according to the second horizontal image distance includes: determining a second FOV of the second camera; reading a height of the right-eye image; and determining the second horizontal actual distance between the right-eye pupil and the second camera according to the vertical actual distance, the second FOV, the second horizontal image distance, and the height of the right-eye image.

For example, determining the actual distance between the pupils of two eyes further includes: acquiring the actual distance between the first camera and the second camera; calculating a sum of the first horizontal actual distance and the second horizontal actual distance; and determining the actual distance between the pupils of two eyes by subtracting the sum of the distances from the actual distance between the first and second cameras.

For example, capturing the at least one eye image includes: capturing an eye image including the monocular pupil and a set marker; extracting the one pupil image position corresponding to the monocular pupil in the at least one eye image, from the at least one eye image, includes: extracting the pupil image position of the monocular pupil in the eye image; and extracting a mark position of the marker from the eye image; and determining the actual distance between the pupils of two eyes according to the one or two pupil image positions includes: determining a horizontal image distance between the monocular pupil and the marker according to the pupil image position of the monocular pupil and the mark position; and determining the actual distance between the pupils of two eyes according to the horizontal image distance between the monocular pupil and the marker.

For example, determining the actual distance between the pupils of two eyes according to the horizontal image distance between the monocular pupil and the marker includes: measuring a vertical actual distance between the two eyes and a camera; determining a FOV of the camera; reading the horizontal image distance between the monocular pupil and the marker; reading a height of the eye image; and determining the actual distance between the pupils of two eyes according to the vertical actual distance between the two eyes and the camera, the FOV, the horizontal image distance between the monocular pupil and the marker, and the height of the eye image.

For example, extracting the one or two pupil image positions corresponding to the monocular pupil or the pupils of two eyes in the at least one eye image, from the at least one eye image, includes: extracting an image area provided with one eye or two eyes from the at least one eye image; obtaining a grayscale image by filtering and graying of the image area; converting the grayscale image into a binary image; finding a boundary of the monocular pupil area or a boundary of the binocular pupil area in the binary image; obtaining one or two elliptical graphics by ellipse fitting of the boundary of the monocular pupil area or the boundary of the binocular pupil area; and taking a center of each elliptical graphic as the image position of corresponding pupil.

For example, the height is a longitudinal pixel size of the image acquired by the camera.

At least one embodiment of the disclosure provides a computer readable storage medium, wherein computer instructions are stored on the computer readable storage medium, and the following operations are implemented when the instructions are executed by a processor: extracting one or two pupil image positions corresponding to a monocular pupil or pupils of two eyes in at least one eye image, from the at least one eye image; and determining an actual distance between the pupils of two eyes according to the one or two pupil image positions.

At least one embodiment of the disclosure provides a wearable ophthalmic device, comprising: a processor and a memory, wherein the memory stores instructions, and the following operations are implemented when the instructions are executed by the processor: extracting one or two pupil image positions corresponding to a monocular pupil or pupils of two eyes in at least one eye image, from the at least one eye image; and determining an actual distance between the pupils of two eyes according to the one or two pupil image positions.

For example, the first camera is configured to capture an eye image including the pupils of two eyes; and the following operations are implemented when the instructions stored in the memory are executed by the processor: determining the pupil image positions of the pupils of two eyes in the eye image; determining an image distance of the pupils of two eyes on the eye image according to the pupil image positions of the pupils of two eyes; and determining the actual distance between the pupils of two eyes according to the image distance of the pupils of two eyes.

For example, the wearable ophthalmic device further comprises a first camera and a second camera, wherein the first camera and the second camera are configured to respectively capture a left-eye image including the left eye and a right-eye image including the right eye; and the following operations are implemented when the instructions stored in the memory are executed by the processor: determining the pupil image position of the left-eye pupil in the left-eye image and the pupil image position of the right-eye pupil in the right-eye image; determining an image position of the first camera in the left-eye image and an image position of the second camera in the right-eye image; determining a first horizontal image distance between the pupil image position of the left-eye pupil and the image position of the first camera in the left-eye image; determining a first horizontal actual distance between the left-eye pupil and the first camera according to the first horizontal image distance; determining a second horizontal image distance between the pupil image position of the right-eye pupil and the image position of the second camera in the right-eye image; determining a second horizontal actual distance between the right-eye pupil and the second camera according to the second horizontal image distance; and determining the actual distance between the pupils of two eyes according to the first horizontal actual distance and the second horizontal actual distance.

For example, the wearable ophthalmic device further comprises a first camera, wherein the first camera is configured to capture an eye image including the monocular pupil and a set marker; and the following operations are implemented when the instructions stored in the memory are executed by the processor: extracting the pupil image position of the monocular pupil in the eye image; extracting a mark position of the marker from the eye image; determining a horizontal image distance between the monocular pupil and the marker according to the pupil image position of the monocular pupil and the mark position; and determining the actual distance between the pupils of two eyes according to the horizontal image distance between the monocular pupil and the marker.

For example, the marker is disposed on a housing of the wearable ophthalmic device.

For example, the wearable ophthalmic device further comprises an infrared source, wherein the infrared source provides a light source for the wearable ophthalmic device to capture an eye image.

The embodiment of the disclosure measures the actual distance between the pupils of two eyes by image processing means, can be further used in other visually related fields such as eye tracking and line of sight (LOS) computing according to the obtained actual distance between the pupils of two eyes, and can further improve the experience effect of a wearer wearing an ophthalmic device (e.g., a VR device).

BRIEF DESCRIPTION OF THE DRAWINGS

In order to clearly illustrate the technical solution of the embodiments of the invention, the drawings of the embodiments will be briefly described in the following; it is obvious that the described drawings are only related to some embodiments of the invention and thus are not limitative of the invention.

FIG. 3C-1 is a schematic diagram of a captured left-eye image in an embodiment of the disclosure;

FIG. 3C-2 is a schematic diagram of a captured right-eye image in an embodiment of the disclosure;

FIG. 3E is a schematic diagram illustrating positions of two eyes and cameras on a plane provided with two eyes in an embodiment of the disclosure;

FIG. 4A is a flowchart of still another interpupillary distance measuring method provided by an embodiment of the disclosure;

FIG. 5 is a flowchart illustrating a process of extracting pupil positions in an embodiment of the disclosure; and FIG. 6 is a composition block diagram of a wearable Ophthalmic device provided by the embodiment of the disclosure.

DETAILED DESCRIPTION

Figure 1:
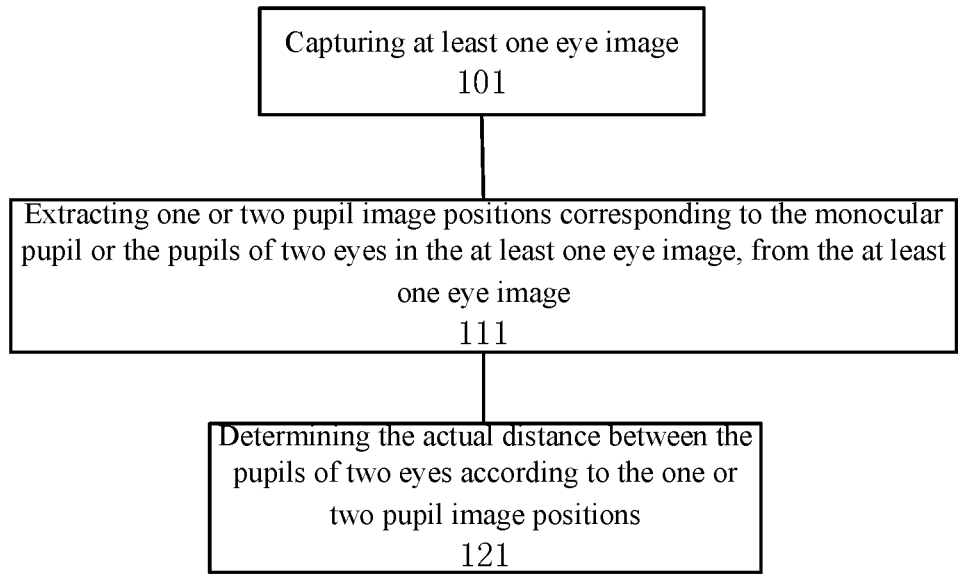
FIG. 1 is a flowchart of an interpupillary distance measuring method provided by an embodiment of the disclosure.

Clear and complete description will be given below to the technical proposals of the embodiments of the disclosure with reference to the accompanying drawings. The preferred embodiments of the disclosure and a variety of characteristics and advantageous details thereof are described more fully with reference to the non-limiting exemplary embodiments illustrated in the accompanying drawings and described below in details. It should be noted that the characteristics illustrated in the figures are not necessary to be drawn to scale. The examples are given only to facilitate an understanding of the implementation of the embodiments of the disclosure, and to enable those skilled in the art to implement the preferred embodiments. Therefore, the examples shall not be construed as limiting the scope of the embodiments of the disclosure.

Unless otherwise specified, the technical terms or scientific terms used in the disclosure shall have normal meanings understood by those skilled in the art. The words "first", "second" and the like used in the disclosure do not indicate the sequence, the number or the importance but are only used for distinguishing different components. In addition, in the embodiments of the disclosure, same or similar reference numerals represent same or similar components.

Description will be given below to an interpupillary distance measuring method, a computer readable storage medium and a wearable ophthalmic device, provided by the disclosure, with reference to the accompanying drawings. In the embodiment of the disclosure, pupil may be adopted to represent eye without causing ambiguity. For instance, the position of the pupil may be used to represent the position of the eye, and the distance between the pupils of two eyes represents the distance between two eyes.

As illustrated in FIG. 1, at least one embodiment of the disclosure provides an interpupillary distance measuring method 100. The interpupillary distance measuring method 100 can comprise: S101: capturing at least one eye image; S111: extracting corresponding one or two pupil image positions of the monocular pupil or the pupils of two eyes in the at least one eye image, from the at least one eye image (namely, extracting one pupil image position corresponding to the monocular pupil, or extracting two pupil image positions corresponding to the pupils of two eyes); and S121: determining the actual distance between the pupils of two eyes according to the one or two pupil image positions.

In some embodiments, the step S101 includes: capturing an image including one eye. In some other embodiments, the step S101 includes: capturing an image simultaneously including two eyes or capturing two images respectively including one eye.

In some embodiments, the image distance of the pupils of two eyes may be extracted from the image in the step S111. In some other embodiments, in the step S111, the distance between the monocular pupil and a set marker may be extracted from the image, or the distance between the monocular pupil and a position point of photographic equipment on the image may be extracted from the image.

In some embodiments, in the step S121, the actual distance between the pupils of two eyes is deduced according to the image distance of the pupils of two eyes obtained in the step S111, in combination with the proportional relationship between graphics. In some other embodiments, in the step S121, the actual distance between the pupils of two eyes is deduced according to the image distance between the monocular pupil and the marker obtained in the step S111, in combination with the proportional relationship between graphics. In some other embodiments, in the step S121, the actual distance between the eye and corresponding photographic equipment may also be deduced according to the image distance in the step S111 and the proportional relationship between graphics, and then the actual distance between the pupils of two eyes is obtained by combining the actual distance between the left eye and the photographic equipment and the actual distance between the right eye and another photographic equipment.

In some embodiments, in order to obtain the actual distance between the pupils according to the image distance relevant to the pupils, a virtual imaging plane on a focal plane (FP) of the photographic equipment is also constructed in the embodiment of the disclosure, wherein in some embodiments, the virtual imaging plane may coincide with an actual imaging plane. If the virtual imaging plane does not coincide with the actual imaging plane, an image formed on the virtual imaging plane and an image captured on the actual imaging plane also satisfy certain proportional relationship, for example, scaling up or down in equal proportion. The computing formula between the image distance relevant to the pupils on the captured image and the actual distance of the pupils may be deduced according to the proportional relationship between similar graphics on the virtual imaging plane and a plane provided with two eyes. Description will be given in the following embodiments by taking the case that the image distance is relevant distance on an image captured on the actual imaging plane as an example.

In some embodiments, in the step S121, the position of the pupil on the image may be extracted from the captured eye image (namely the image disposed on the actual imaging plane) by the method as illustrated in FIG. 5. The distance relevant to the pupil on the captured image may be further obtained according to the position of the pupil on the captured image. For instance, the distance of the pupils of two eyes on the captured image is determined according to the pupil positions extracted from the captured image. For instance, the first horizontal image distance or the second horizontal image distance is determined according to the pupil position extracted from the captured image and corresponding position of a camera. For instance, the horizontal image distance is determined according to the pupil position extracted from the captured image and the position of a marker.

In some embodiments, when a user begins to use a wearable device such as a VR device, the user will do some operations on the start interface to enter the main interface, for example, clicking on a menu or the like, or enter the main interface only in a certain initialization phase. At this point, the interpupillary distance measuring method provided by the disclosure can be activated to measure the actual distance between the pupils.

Figure 2A:
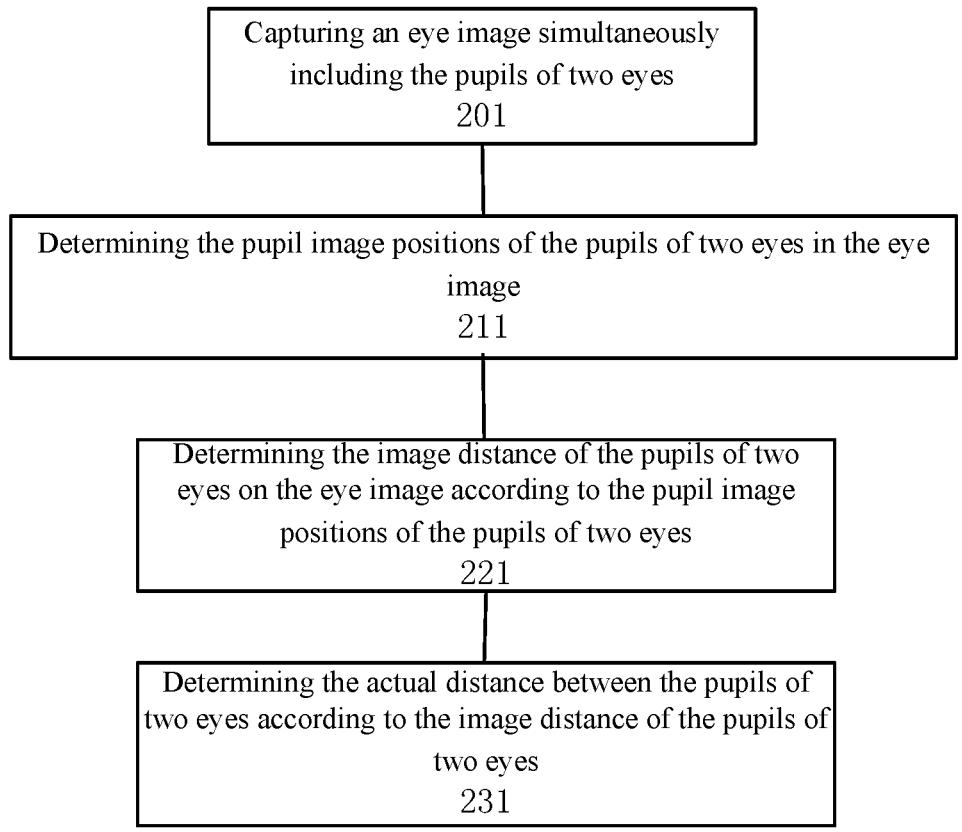
FIG. 2A is a flowchart of another interpupillary distance measuring method provided by an embodiment of the disclosure.

As illustrated in FIG. 2A, another interpupillary distance measuring method 200 is provided. An image in the interpupillary distance measuring method 200 may be a binocular image captured by one camera. For instance, the interpupillary distance measuring method 200 can comprise: S201: capturing an eye image simultaneously including the pupils of two eyes; S211: determining the pupil image positions of the pupils of two eyes in the eye image; S221: determining the image distance of the pupils of two eyes on the eye image according to the pupil image positions of the pupils of two eyes; and S231: determining the actual distance between the pupils of two eyes according to the image distance of the pupils of two eyes.

In some embodiments, in the step S201, an infrared camera may be adopted to capture two eyes of the user, and meanwhile, a plurality of infrared LED lights may be adopted to provide light sources for the infrared camera. When the camera captures images, it is necessary to ensure that the user's two eyes can be captured, that is, to ensure that the camera can work normally and the LED lights can be turned on normally. Of course, the embodiment of the disclosure may also adopt cameras of other types and light sources of other types for shooting. No limitation will be given here in the disclosure.

Figure 2B:
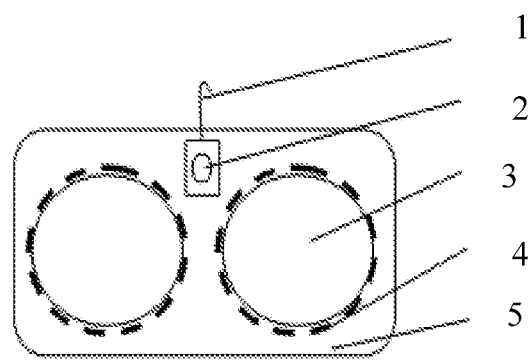
FIG. 2B is a schematic diagram of an interpupillary distance measuring device provided by an embodiment of the disclosure.

As illustrated in FIG. 2B, in some embodiments, the interpupillary distance measuring method may be applied in a VR device; corresponding infrared LED lights 4 use infrared light to illuminate the inside of the VR device; and the LED lights 4 are arranged on the periphery of a lens 3 used by the VR device and may also be distributed on an inner housing 5 of the VR device. The number of the LED lights 4 is enough to illuminate the inside of the VR device and take a clear photo of the eye image. The camera 2 is disposed at the upper middle position of the VR device. The VR device may further include an interface 1. The interface 1 may be connected with the infrared camera 2 and data processing equipment. For instance, the interface 1 may be a USB interface (connected with an outer computer), an MIPI interface (connected with a mobile terminal), a WIFI interface, a Bluetooth interface, etc.

Figure 2C:
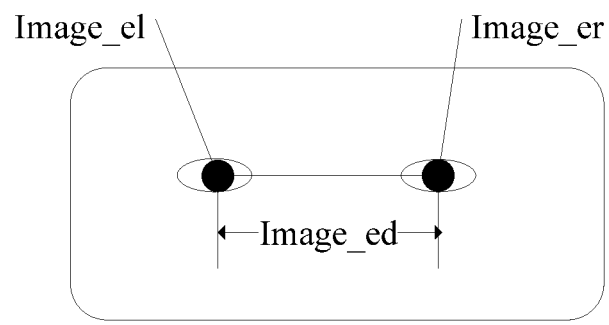
FIG. 2C is a schematic diagram of a binocular image captured by a camera in an embodiment of the disclosure.

Supposing the pixel size of an image actually captured by the camera is "Image_W*Image_H", as illustrated in FIG. 2C, by analysis of the captured image (namely the image in FIG. 2C), the position of the left-eye pupil on the image is Image_el; the position of the right-eye pupil on the image is Image_er; and the spacing between the left-eye pupil and the right-eye pupil on the captured image (namely the distance of the pupils of two eyes on the image) is Image_ed.

Figure 2D:
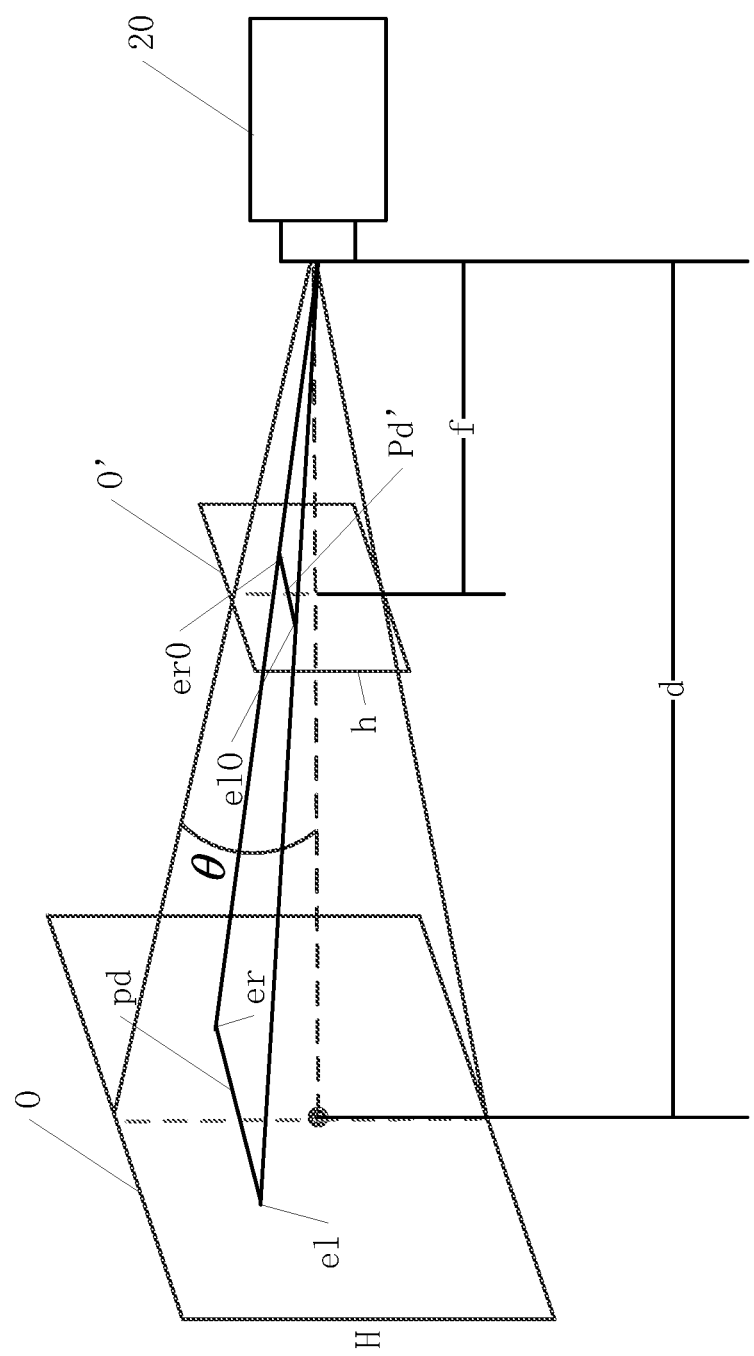
FIG. 2D is a schematic diagram of similar graphics in the embodiment of the disclosure.

The actual distance between the pupils of two eyes is obtained according to the image distance Image_ed of the pupils of two eyes on the captured image, and further reference is made to relevant position points as illustrated in FIG. 2D and the constructed relevant plane. FIG. 2D shows two planes, respectively a virtual imaging plane O' (namely an FP) and a plane O provided with the two eyes. Supposing the focal length of a camera 20 is f, the field of view (FOY) of the camera 20 is 2*θ. The positions el0 and er0 of the pupils of two eyes are illustrated in the virtual imaging plane O'. The actual positions el and er of left and right eyes are illustrated in the actual pane O provided with the pupils of two eyes. In FIG. 2D, the position of the eye is used to represent the position of the pupil of the eye. H refers to the height of the plane provided with the two eyes, and for example, the parameter H may be obtained by calculation of the FOV of the camera; h refers to the height of the FP, and for example, the parameter h may also be obtained by calculation of the FOV of the camera; pd (namely the actual distance between the pupils of two eyes) refers to the actual interpupillary distance between the left-eye pupil el and the right-eye pupil er in FIG. 2D on the plane O; and pd' (namely the distance of the pupils of two eyes on the FP O') refers to the distance between the pupils of two eyes er0 (corresponding to the point er on the plane O) and el0 (corresponding to the point el on the plane O) on the imaging plane O'.

The following formulas may be obtained from the perspective relationship of FIG. 2D:

$\tan(\theta) = (h/2)/f;$ $\tan(\theta) = (H/2)/d;$ $Image\_ed/pd' = Image\_H/h;$ $pd/pd' = H/h.$ The actual distance between the pupils of two eyes of the user $pd = 2*d*\tan(\theta)*Image\_ed/Image\_H$ may be obtained according to the above relational expressions.

In some embodiments, the step of determining the actual distance pd between the pupils of two eyes according to the image distance Image_ed of the pupils of two eyes in S221 in FIG. 2A may include: measuring the vertical actual distance d between the two eyes and the cameras (for instance, the vertical distance between the plane O provided with the two eyes and the camera 20 as illustrated in FIG. 2D); determining the FOV θ of the camera (for instance, the FOV of the camera as illustrated in FIG. 2D); reading the image distance Image_ed of the pupils of two eyes (for instance, the image distance between the left-eye pupil and the right-eye pupil on the captured image as illustrated in FIG. 2C); reading the height Image_H of the eye image (for instance, longitudinal pixels of the captured image in FIG. 2C); and determining the actual distance pd between the pupils of two eyes (namely the distance between er and el in FIG. 2D) according to the image distance Image_ed of the pupils of two eyes, the FOV θ, the vertical actual distance d between the two eyes and the cameras, and the height Image_H of the eye image.

The embodiment of the disclosure adopts an infrared camera to capture the user's two eyes, measures the distance of the pupils of two eyes on the image by image processing means, and then calculates the actual distance between the pupils. After the interpupillary distance is detected, the embodiment of the disclosure may also be applied in eye tracking, line of sight (LOS) computing and other fields relevant to eyes.

Figure 3A:
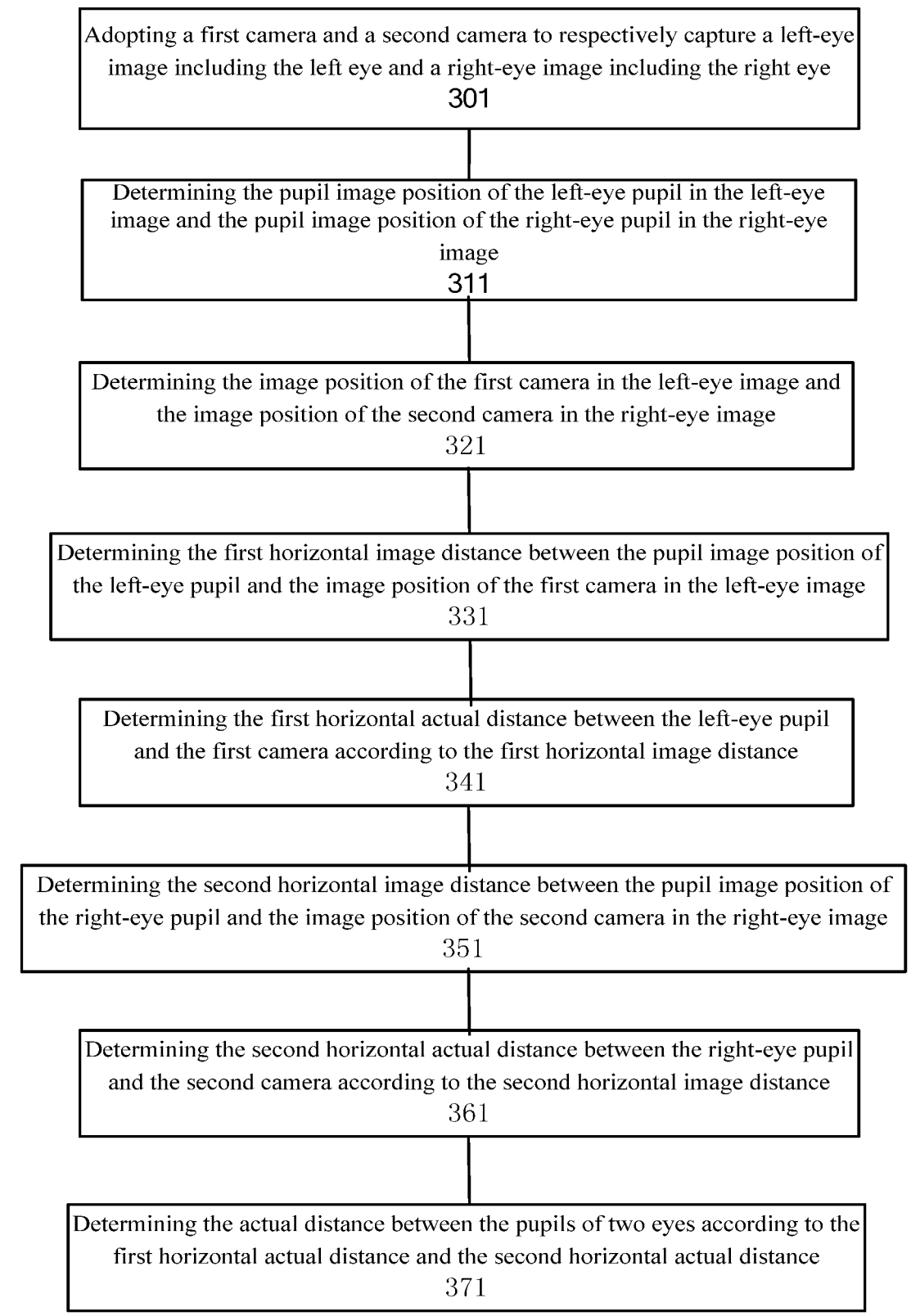
FIG. 3A is a flowchart of still another interpupillary distance measuring method provided by an embodiment of the disclosure.

As illustrated in FIG. 3A, the embodiment of the disclosure provides an interpupillary distance measuring method 300. The interpupillary distance measuring method 300 can comprise: S301: adopting a first camera and a second camera to respectively capture a left-eye image including the left eye and a right-eye image including the right eye; S311: determining the pupil image position of the left-eye pupil in the left-eye image and the pupil image position of the right-eye pupil in the right-eye image; S321: determining the image position of the first camera in the left-eye image and the image position of the second camera in the right-eye image; S331: determining the first horizontal image distance between the pupil image position of the left-eye pupil and the image position of the first camera in the left-eye image; S341: determining the first horizontal actual distance Sep_1 between the left-eye pupil and the first camera according to the first horizontal image distance; S351: determining the second horizontal image distance between the pupil image position of the right-eye pupil and the image position of the second camera in the right-eye image; S361: determining the second horizontal actual distance between the right-eye pupil and the second camera according to the second horizontal image distance; and S371: determining the actual distance between the pupils of two eyes according to the first horizontal actual distance and the second horizontal actual distance.

Figure 3B:
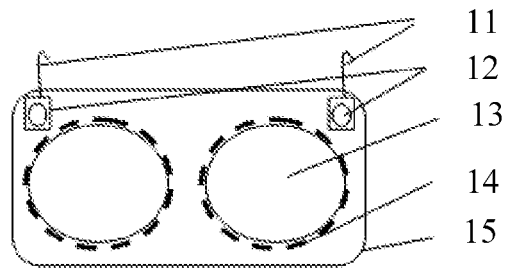
FIG. 3B is another schematic diagram of the interpupillary distance measuring device provided by an embodiment of the disclosure.

In some embodiments, in the step S301, a device as illustrated in FIG. 3B may be adopted to capture images. For instance, two infrared cameras 11 (namely the first camera and the second camera respectively disposed above the left eye and the right eye) may be utilized to measure the distance between the pupils; the position between the two infrared cameras 11 is known; and each infrared camera 11 can respectively capture one eye of the user. Meanwhile, a plurality of infrared LED lights 14 are provided. The LED lights 14 provide light sources for the two infrared cameras. As illustrated in FIG. 3B, the two cameras 11 are respectively disposed above lenses 13, and the two cameras 11 are in the same horizontal line. Of course, the embodiment of the disclosure may also adopt cameras of other types and light sources of other types for shooting. No limitation will be given here in the disclosure.

For instance, the lens 13 in FIG. 3B may be a lens used by the VR device, and the infrared LED lights 14 adopt infrared light to illuminate the inside of the VR device. The LED lights 14 are usually disposed on the periphery of the lens 13 of the VR device and may also be distributed on an inner housing 15 of the VR device. The number of the LED lights 14 is enough to illuminate the inside of the VR device and take a photo of the eye image.

Figures 1, 3C:
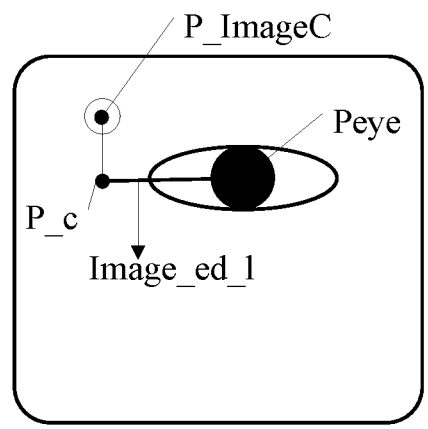
Figures 2, 3C:
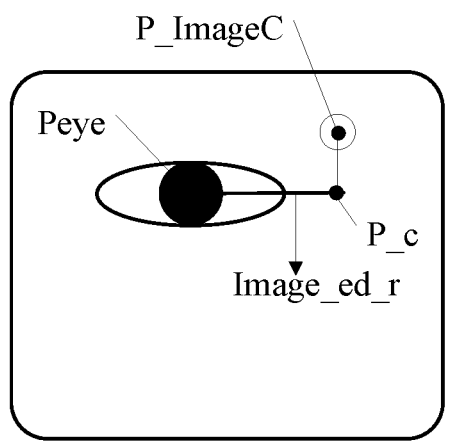

Images captured by one camera 12 in FIG. 3B may be as illustrated in FIGS. 3C-1 and 3C-2.

The pixel size of the captured images of the left eye and the right eye as illustrated in FIGS. 3C-1 and 3C-2 is Image_W*Image_H, and the image center is P_ImageC (namely corresponding position of the camera 12 on an image captured on the actual imaging plane). The position of the monocular pupil center on the captured image is point Peye, and a transverse extension line of the point Peye and a longitudinal extension line of point P_ImageC are intersected at point P_c. The distance between the point Peye and the point P_c is the first horizontal image distance Image_ed_l or the second horizontal image distance Image_ed_r.

Figure 3D:
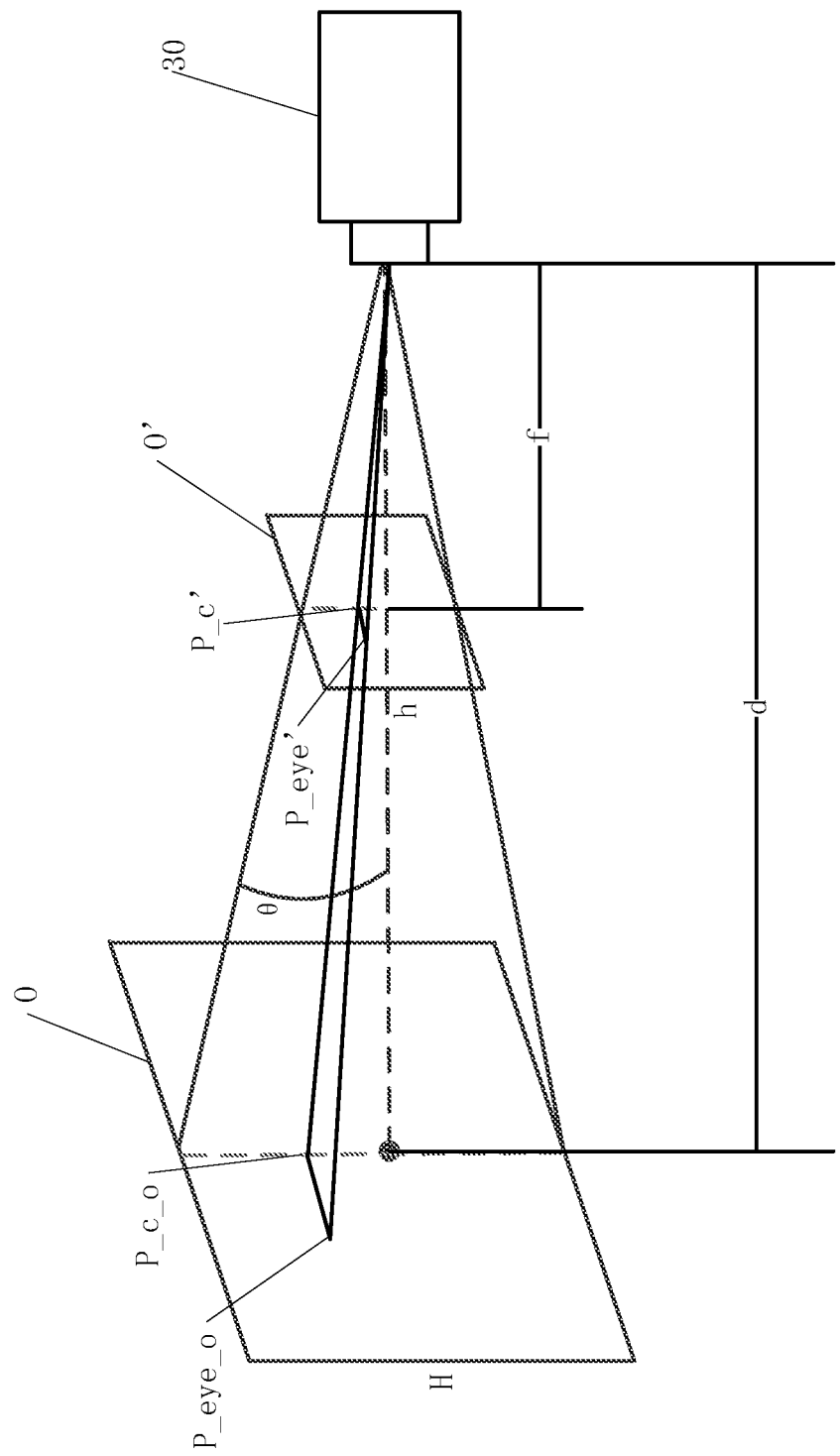
FIG. 3D is a schematic diagram of similar graphics in an embodiment of the disclosure.

In order to calculate the actual distance between the pupils of two eyes according to the first horizontal image distance and the second horizontal image distance, further reference can be made to relevant position points as illustrated in FIG. 3D and the constructed relevant plane.

FIG. 3D illustrates two planes which are respectively a virtual imaging plane O' (namely an FP) and a plane O provided with the two eyes. The points P_eye_o and P_c_o in FIG. 3D are respectively corresponding position points of the points Peye and P_c on the captured image on the plane O provided with the two eyes. The points P_eye_o and P_c_o in FIG. 3D respectively correspond to the points Peye' and P_c' in the virtual imaging plane O'. Supposing the FP is an actual imaging plane, the first horizontal image distance or the second horizontal image distance on the captured image may be represented as Image_ed.x'=P_c'.x−eye'.x, in which the parameter x may be l(left) or r(right) which respectively indicate the first horizontal image distance (for instance, Image_ed.l'=P_c'.l−Peye'.l) corresponding to the left eye and the second horizontal image distance (for instance, Image_ed.r'=P_c'−Peye'.r) corresponding to the right eye. In actual condition, the point Peye' may be on the left of the point P_c' and may also be on the right of the point P_c', so the first horizontal image distance Image_ed.l' or the second horizontal image distance Image_ed.r' may be positive or negative.

Supposing the focal length of the first camera and a second camera 30 in FIG. 3D is f, the FOV is 2*θ; the height of the virtual imaging plane O' is h; the vertical actual distance from the human eye to the camera is d; P_eye_o refers to the position of the human eye on the plane O; and P_c_o refers to a projection of the point P_c' on the plane O. The distance between the point P_eye_o and the point P_c_o is the first horizontal actual distance or the second horizontal actual distance Sep_x (in which the parameter x may be l or r which respectively indicates the first horizontal actual distance Sep_l corresponding to the left eye and the second horizontal actual distance Sep_r corresponding to the right eye).

The following formulas may be obtained from the perspective relationship as illustrated in FIG. 3D:

$$\tan(\theta)=(h/2)/f$$

$$\tan(\theta)=(H/2)/d$$

$$\text{Image\_}ed/\text{Image\_}ed'=\text{Image\_}H/h;$$

$$\text{Sep\_}X/\text{Image\_}ed'=H/h$$

According to the above relational expressions, the computing formula of the first or second horizontal actual distance of the user may be: Sep_x=2*d*tan(θ*Image_ed/Image_H.

The transverse distance Image_ed_l from the pupil to the image center of the camera on the image may be obtained according to the left-eye image captured by the first camera, and is then substituted into the above formula to obtain the first horizontal actual distance Sep_l=2*d*tan(θ)*Image_ed_l/Image_H.

Similarly, as for the second camera, the second horizontal actual distance Sep_r=2*d*tan(θ)*Image_ed_r/Image_H may be obtained.

After the first horizontal actual distance and the second horizontal actual distance are obtained by the above method, the actual distance between the pupils of two eyes may be calculated by further reference to FIG. 3E. As illustrated in FIG. 3E, if the distance of two cameras (the first camera and the second camera) on the VR device is known to be Sep, the left-eye image of the user is captured by the first camera 12 by image processing means (for example, as illustrated in FIG. 5), and the horizontal distance Sep_l from the left-eye pupil to a corresponding point of the first camera on the captured image is obtained by calculation; and the distance Sep_r from corresponding point of the second camera 12 to the center of the right-eye pupil on the captured image may be calculated by the same method. Thus, the actual distance between the pupils of two eyes of the user is pd=Sep−Sep_l−−Sep_r.

In some embodiments, the step of determining the first horizontal actual distance in S341 can include: measuring the vertical actual distance d between the first camera and the second camera and the two eyes (for instance, the vertical distance between the plane O provided with the two eyes and the camera 30 as illustrated in FIG. 3D); determining the first FOV θ of the first camera (for instance, the FOV of the camera 30 as illustrated in FIG. 3D); reading the height of the left-eye image (for instance, longitudinal shooting pixels of the image in FIG. 3C-1); and determining the first horizontal actual distance Sep_l between the left-eye pupil and the first camera (as illustrated in FIG. 3E) according to the vertical actual distance d, the first FOV θ, the first horizontal image distance Image_ed_l (for instance, the distance between the left-eye pupil and a projective point P_ImageC of the first camera 12 on the image as illustrated in FIG. 3C-1), and the height of the left-eye image. The step of determining the second horizontal actual distance in S361 can include: determining the second FOV θ of the second camera; reading the height of the right-eye image (for instance, longitudinal shooting pixels of the image in FIG. 3C-2); and determining the second horizontal actual distance Sep_r between the right-eye pupil and the second camera (as illustrated in FIG. 3E) according to the vertical actual distance d, the second FOV θ, the second horizontal image distance Image_ed_r (for instance, the distance between the right-eye pupil and a projective point P_ImageC of the second camera 12 on the image as illustrated in FIG. 3C-2), and the height of the right-eye image.

As illustrated in FIG. 3E, in some embodiments, the step of determining the actual distance between the pupils of two eyes in S371 may further include: acquiring the actual distance Sep between the first and second cameras; calculating the sum of the first horizontal actual distance Sep_l and the second horizontal actual distance Sep_r; and determining the actual distance between the pupils of two eyes by subtracting the sum of the distances from the actual distance between the first and second cameras. On the VR device, the distance Sep between the first and second cameras is known, so the interpupillary distance of the user is: pd=Sep−(Sep_l+Sep_r).

In summary, the distance of the two cameras on the VR device is known to be Sep; the left-eye image of the user is captured by the first camera camera_l by image processing method; the horizontal distance Sep_l from the left-eye pupil to the left camera is obtained by calculation; and the distance from the second camera camera_r to the center of the right-eye pupil may be calculated by the same method. Thus, the final interpupillary distance of the user is: pd=Sep−Sep_l−Sep_r, as illustrated in FIG. 3E.

A monocular image is respectively captured by two infrared cameras with known positions; each camera can capture one eye of the user; and meanwhile, a plurality of infrared LED lights are also adopted to provide light sources for the infrared cameras. For instance, two infrared cameras in a VR device are utilized to respectively capture one eye of the user; the distance from the monocular pupil on the captured image to a corresponding point of the center of corresponding camera on the image is measured by image processing means; and then the actual distance between the pupils is calculated. The camera used in the embodiment of the disclosure may also be applied in eye tracking, LOS computing or other working fields relevant to eyes after detecting the interpupillary distance.

As illustrated in FIG. 4A, an interpupillary distance measuring method 400 is provided. The interpupillary distance measuring method 400 comprises: S401: capturing an eye image including the monocular pupil and a set marker; S411: extracting the pupil image position of the monocular pupil in the eye image, and extracting the mark position of the marker from the eye image; S421: determining the horizontal image distance between the monocular pupil and the marker according to the pupil image position of the monocular pupil and the mark position; and S431: determining the actual distance between the pupils of two eyes according to the horizontal image distance between the monocular pupil and the mark position.

Figure 4B:
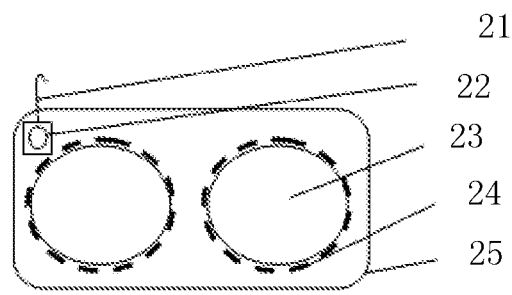
FIG. 4B is still another schematic diagram of the interpupillary distance measuring device provided by an embodiment of the disclosure.

As illustrated in FIG. 4B, in some embodiments, the interpupillary distance measuring method 400 may be applied to a VR device. The VR device is equipped with a single infrared camera 22 and infrared LED lights 24. When the VR device is used, infrared sources of the LED lights 24 illuminate the human eyes; the infrared camera 22 captures one eye of the user and a marker 26 on a VR housing 25; the pupil of the user and the marker 26 are obtained by image processing method; and the actual distance between the pupils of two eyes is estimated according to the transverse distance from the pupil to the marker on the image. For instance, the marker 26 may be disposed on the housing 25 of the VR device. Of course, the embodiment of the disclosure may also adopt other types of cameras and other types of light sources for shooting. No limitation will be given here in the disclosure.

For instance, the VR device uses a lens 23, and the infrared LED lights 24 utilize infrared light to illuminate the inside of the VR device. The LED lights 24 are usually disposed on the periphery of the lens 23 and may also be distributed on an inner housing 25 of the VR device. The number of the LED lights 24 is enough to illuminate the inside of the VR device and take a photo of the eye image. In general, 8 LED lights are adopted.

Figure 4C:
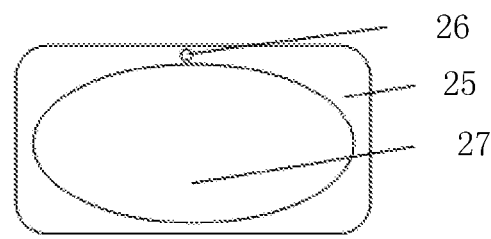
FIG. 4C is a schematic diagram illustrating a position of a marker in an embodiment of the disclosure.
Figure 4D:
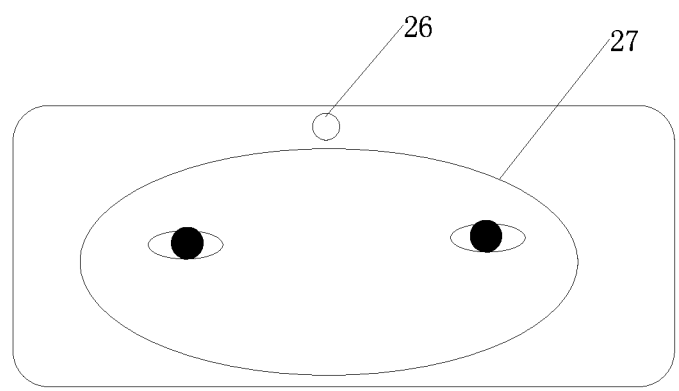
FIG. 4D is a relation diagram illustrating a relative position of two eyes and a marker in an embodiment of the disclosure.

As illustrated in FIGS. 4C and 4D, the marker 26 is disposed above a viewing window 27 of the VR device. For instance, the marker 26 is disposed in the middle of the left and right direction of the VR housing 25. When the VR device is normally used by the user, the marker 26 may be disposed at the center of the user's binocular spacing. For instance, the marker 26 may be an object point similar to the infrared LED lights 24 and the like that can be identified by the infrared camera. The viewing window 27 of the VR device refers to a window through which the user can view the content displayed by the VR device through the lens 23.

Figure 4E:
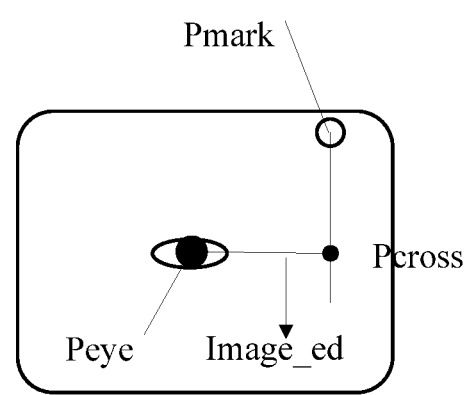
FIG. 4E is an image of a monocular pupil and a marker, captured by the camera, in an embodiment of the disclosure.

The image captured by the camera is as illustrated in FIG. 4E. The captured image includes the position point Peye of one eye and the marker Pmark.

Supposing the pixel size of the image (as illustrated in FIG. 4E) captured by the camera is Image_W*Image_H, the position of the monocular pupil center on the image is Peye, and the point of the marker on the image is Pmark. A transverse extension line of the point Peye and a longitudinal extension line of the point Pmark, on the image, are intersected at point Pcross. The distance between the point Peye and the point Pcross is the horizontal image distance Image_ed.

Figure 4F:
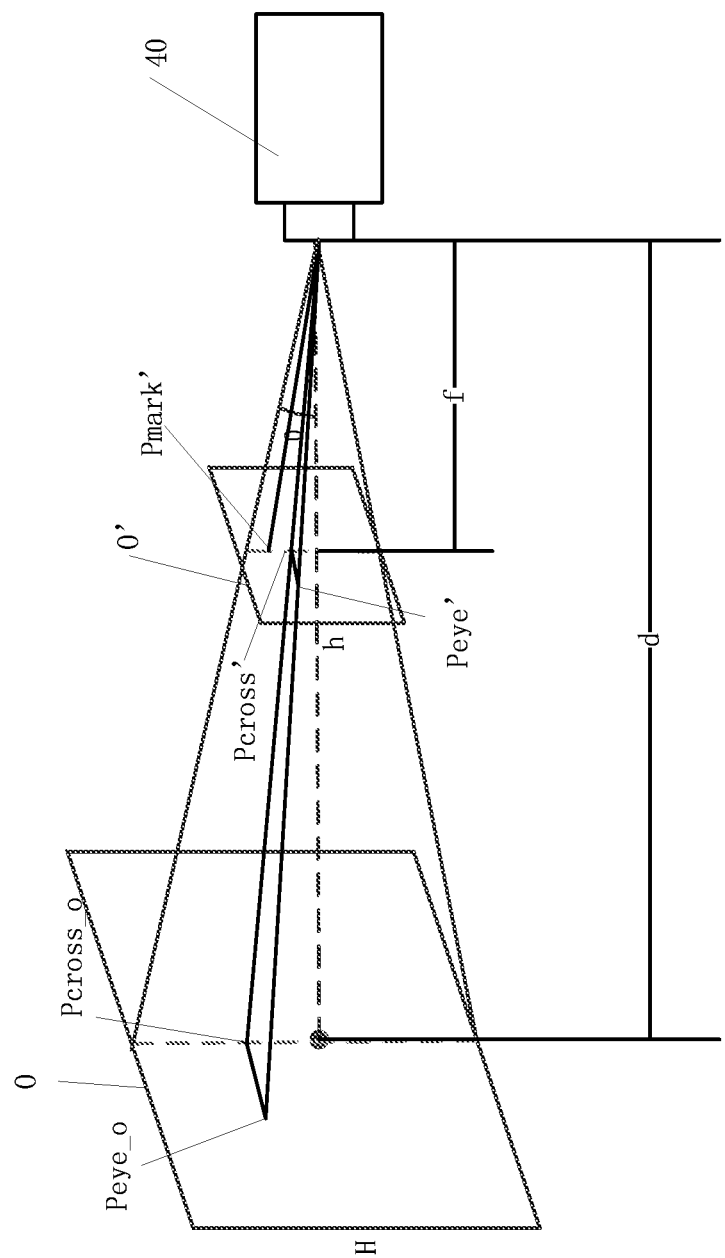
FIG. 4F is a schematic diagram of similar graphics in an embodiment of the disclosure.

In order to deduce the computing formula between the horizontal image distance between the point Peye and the point Pcross and the actual distance between the pupils, further reference can be made to relevant position points as illustrated in FIG. 4F and the constructed relevant plane.

FIG. 4F illustrates two planes which are respectively a virtual imaging plane O' disposed on an FP, and a plane O provided with the pupils of two eyes. The points Peye, Pmark and Pcross on the captured image respectively correspond to points Peye', Pmark' and Pcross' on the virtual imaging plane O'. The position Peye' of the monocular pupil and the position Pmark' of the marker are illustrated in the virtual imaging plane O'. The distance from the human eye to the camera is d. Peye_o refers to the position of the human eye on the plane O, and Pcross_o refers to a projection of Pcross' on the plane O. Correspondingly, the distance between Peye_o and Pcross_o is half of the actual distance between the pupils of two eyes. The focal length of the camera 40 is f, and the FOV is θ. H refers to the height of the plane provided with the two eyes, and for example, H may be obtained by calculating the FOV of the camera; and h refers to the height of the FP, and for example, h may be obtained by calculating the FOV of the camera.

The following formulas may be obtained from the perspective relationship in FIG. 4E:

$$\tan(\theta)=(h/2)/f;$$

$$\tan(\theta)=(H/2)/d;$$

$$\text{Image\_}ed/pd'=\text{Image\_}H/h;$$

$$pd/pd'=H/h.$$

According to the above relational expressions, pd'=2*d*tan(θ)*Image_ed/Image_H may be obtained. The distance between the pupils of two eyes of the user is pd=2*pd'.

In some embodiments, the step S421 may include: measuring the vertical actual distance d between the two eyes and the cameras (for instance, the vertical distance between the plane O provided with the two eyes and a camera 40 as illustrated in FIG. 4F); determining the FOV θ of the camera (for instance, the FOV of the camera 40 as illustrated in FIG. 4F); reading the horizontal image distance Image_ed between the monocular pupil and the marker on the captured image (for instance, the distance between the monocular pupil and the marker on the image as illustrated in FIG. 4E); reading the height of the eye image of the captured image (for instance, longitudinal pixels of the image as illustrated in FIG. 4E); and determining the actual distance (namely pd) between the pupils of two eyes according to the vertical actual distance d between the two eyes and the cameras, the FOV θ, the horizontal image distance Image_ed between the monocular pupil and the marker, and the height Image_H of the eye image.

As illustrated in FIG. 5, for instance, the step of extracting the corresponding one or two pupil image positions of the monocular pupil and the pupils of two eyes in the at least one eye image, from the at least one eye image, in the above three embodiments, may include: S501: extracting an image area provided with one eye or two eyes from respective eye image; S511: obtaining a grayscale image by filtering and graying of the image area, and converting the grayscale image into a binary image; S521: finding the boundary of the monocular pupil area or the boundary of the binocular pupil area in the binary image; S531: obtaining one or two elliptical graphics by ellipse fitting of the boundary of the monocular pupil area or the boundary of the binocular pupil area; and S541: taking the center of the elliptical graphic as the image position of corresponding pupil. Of course, the image position of the pupil may also be obtained by other methods. No limitation will be given here in the disclosure.

The height of the eye image in the above embodiment may be the longitudinal pixel size of the image captured by the camera.

In some embodiments, the marker may be extracted after the image acquired by the camera is obtained. The process of extracting the marker from the image may include the following steps: (1) marker area extraction (for instance, extracting an approximate area provided with the marker from the entire image): as the position of the marker in the image is almost determined after the user puts on the VR device, a large image area may be selected as a target area of the area provided with the marker; (2) image filtering: performing filtering, e.g., Gaussian filtering, on the extracted image; (3) graying: performing graying on the filtered image, and converting an RGB image into a grayscale image; (4) threshold processing: the grayscale image is converted into a binary image, and as the marker itself is an infrared LED light, the marker is a white spot on the image captured by the infrared camera, so a large threshold may be set, e.g., the threshold=240, and then image binaryzation is performed; (5) marker area inspection: finding the boundary of the marker area by utilization of morphological method; (6) marker ellipse fitting: obtaining ellipses by ellipse fitting of the boundary of the marker area; and (7) marker center output: the marker position is the center of the ellipse.

The embodiment of the disclosure provides a method for estimating the interpupillary distance by utilization of a single infrared camera. For instance, one infrared camera and a plurality of LED lights may be adopted. The single camera can capture one eye of the user and the marker on the VR housing. The plurality of infrared LED lights provide light sources for the infrared camera. The infrared camera in the VR device is utilized to capture one eye of the user and the marker on the VR housing; the transverse distance between the monocular pupil and the marker is measured by image processing means; and then the actual distance between the pupils of two eyes is calculated. The camera used in the embodiment of the disclosure may also be applied to eye tracking, LOS computing or other working fields relevant to eyes after detecting the interpupillary distance.

At least one embodiment of the disclosure provides a computer readable storage medium. Computer instructions are stored on the computer readable storage medium. The following operations are implemented when the instructions are executed by a processor: extracting corresponding one or more pupil image positions of the monocular pupil and the pupils of two eyes in at least one eye image, from the at least one eye image; and determining the actual distance between the pupils of two eyes according to the one or two pupil image positions.

FIG. 6 is a block diagram of a wearable ophthalmic device 600 provided by the disclosure. The wearable ophthalmic device 600 can comprise: a processor 602 and a memory 603. The memory 603 stores instructions. The following operations are implemented when the instructions are executed by the processor 602: extracting corresponding one or more pupil image positions of the monocular pupil and the pupils of two eyes in at least one eye image, from the at least one eye image; and determining the actual distance between the pupils of two eyes according to the one or two pupil image positions.

In some embodiments, the wearable ophthalmic device 600 can further comprise: at least one camera 601. For instance, the at least one camera 601 is configured to capture the at least one eye image.

In some embodiments, the wearable ophthalmic device 600 can further comprise: at least one infrared source 604. The infrared source 604 may be configured to provide a shooting light source for the at least one camera 601.

In some embodiments, the wearable ophthalmic device 600 can include basic components of VR glasses. For instance, the basic components of the VR glasses can include lenses, a housing, etc.

In some embodiments, the at least one camera 601 includes a first camera, in which the first camera is configured to: capture an eye image including the pupils of two eyes. The following operations are implemented when the instructions stored in the memory are executed by the processor: determining the pupil image positions of the pupils of two eyes in the eye image; determining the image distance of the pupils of two eyes on the eye image according to the pupil image positions of the pupils of two eyes; and determining the actual distance between the pupils of two eyes according to the image distance of the pupils of two eyes.

In some embodiments, the at least one camera 601 can further include a first camera and a second camera, in which the first camera and the second camera are configured to respectively capture a left-eye image including the left eye and a right-eye image including the right eye. The following operations are implemented when the instructions stored in the memory 603 are executed by the processor 602: determining the pupil image position of the left-eye pupil in the left-eye image and the pupil image position of the right-eye pupil in the right-eye image; determining the image position of the first camera in the left-eye image and the image position of the second camera in the right-eye image; determining the first horizontal image distance between the pupil image position of the left-eye pupil and the image position of the first camera in the left-eye image; determining the first horizontal actual distance between the left-eye pupil and the first camera according to the first horizontal image distance; determining the second horizontal image distance between the pupil image position of the right-eye pupil and the image position of the second camera in the right-eye image; determining the second horizontal actual distance between the right-eye pupil and the second camera according to the second horizontal image distance; and determining the actual distance between the pupils of two eyes according to the first horizontal actual distance and the second horizontal actual distance.

In some embodiments, the camera 601 can further include a first camera, in which the first camera is configured to capture an eye image including the monocular pupil and a set marker. The following operations are implemented when the instructions stored in the memory 603 are executed by the processor 602: extracting the pupil image position of the monocular pupil in the eye image; extracting the mark position of the marker from the eye image; determining the horizontal image distance between the monocular pupil and the marker according to the pupil image position of the monocular pupil and the mark position; and determining the actual distance between the pupils of two eyes according to the horizontal image distance between the monocular pupil and the marker. For instance, the marker is disposed on the housing of the wearable ophthalmic device.

In some embodiments, the memory 603 and the processor 602 may be disposed on the same PC or other processing equipment.

As illustrated in FIGS. 1-5, similar description on the wearable ophthalmic device 600 will not be further described here.

The foregoing is only the preferred embodiments of the disclosure and not intended to limit the scope of protection of the disclosure. Any change or replacement that may be easily thought of by those skilled in the art within the technical scope disclosed by the disclosure shall fall within the scope of protection of the disclosure. Therefore, the scope of protection of the disclosure shall be defined by the appended claims.

The application claims priority to the Chinese patent application No. 201710551489.5, filed Jul. 7, 2017, the disclosure of which is incorporated herein by reference as part of the application.

The invention claimed is:

1. An interpupillary distance measuring method, comprising:
   capturing at least one eye image;
   extracting one pupil image position corresponding to a monocular pupil from one eye image including one eye, or extracting two pupil image positions corresponding to pupils of two eyes from two eye images each of which includes one eye; and
   determining an actual distance between the pupils of two eyes according to the one or two pupil image positions, wherein
   capturing the at least one eye image includes: adopting a first camera and a second camera to respectively capture a left-eye image including a left eye and a right-eye image including a right eye;
   extracting the one pupil image position corresponding to the monocular pupil in the at least one eye image, from the at least one eye image, includes: determining the pupil image position of the left-eye pupil in the left-eye image and the pupil image position of the right-eye pupil in the right-eye image; and
   determining the actual distance between the pupils of two eyes according to the one or two pupil image positions includes:
   determining an image position of the first camera in the left-eye image and an image position of the second camera in the right-eye image;
   determining a first horizontal image distance between the pupil image position of the left-eye pupil and the image position of the first camera in the left-eye image;
   determining a first horizontal actual distance between the left-eye pupil and the first camera according to the first horizontal image distance;
   determining a second horizontal image distance between the pupil image position of the right-eye pupil and the image position of the second camera in the right-eye image;
   determining a second horizontal actual distance between the right-eye pupil and the second camera according to the second horizontal image distance; and
   determining the actual distance between the pupils of two eyes according to the first horizontal actual distance and the second horizontal actual distance.

2. The interpupillary distance measuring method according to claim 1, wherein determining the first horizontal actual distance between the left-eye pupil and the first camera according to the first horizontal image distance includes:
measuring a vertical actual distance between the first camera and the second camera and the two eyes;
determining a first FOV of the first camera;
reading a height of the left-eye image; and
determining the first horizontal actual distance between the left-eye pupil and the first camera according to the vertical actual distance, the first FOV, the first horizontal image distance, and the height of the left-eye image; and
determining the second horizontal actual distance between the right-eye pupil and the second camera according to the second horizontal image distance includes:
determining a second FOV of the second camera;
reading a height of the right-eye image; and
determining the second horizontal actual distance between the right-eye pupil and the second camera according to the vertical actual distance, the second FOV, the second horizontal image distance, and the height of the right-eye image.

3. The interpupillary distance measuring method according to claim 2, wherein the height is a longitudinal pixel size of the image acquired by the camera.

4. The interpupillary distance measuring method according to claim 1, wherein
determining the actual distance between the pupils of two eyes further includes:
acquiring the actual distance between the first camera and the second camera;
calculating a sum of the first horizontal actual distance and the second horizontal actual distance; and
determining the actual distance between the pupils of two eyes by subtracting the sum of the distances from the actual distance between the first and second cameras.

5. The interpupillary distance measuring method according to claim 1, wherein extracting the one or two pupil image positions corresponding to the monocular pupil or the pupils of two eyes in the at least one eye image, from the at least one eye image, includes:
extracting an image area provided with one eye or two eyes from the at least one eye image;
obtaining a grayscale image by filtering and graying of the image area;
converting the grayscale image into a binary image;
finding a boundary of the monocular pupil area or a boundary of the binocular pupil area in the binary image;
obtaining one or two elliptical graphics by ellipse fitting of the boundary of the monocular pupil area or the boundary of the binocular pupil area; and
taking a center of each elliptical graphic as the image position of corresponding pupil.

6. An interpupillary distance measuring method, comprising:
capturing at least one eye image;
extracting one pupil image position corresponding to a monocular pupil from one eye image including one eye, or extracting two pupil image positions corresponding to pupils of two eyes from two eye images each of which includes one eye; and
determining an actual distance between the pupils of two eyes according to the one or two pupil image positions, wherein
capturing the at least one eye image includes: capturing an eye image including the monocular pupil and a set marker;
extracting the one pupil image position corresponding to the monocular pupil in the at least one eye image, from the at least one eye image, includes:
extracting the pupil image position of the monocular pupil in the eye image; and
extracting a mark position of the marker from the eye image; and
determining the actual distance between the pupils of two eyes according to the one or two pupil image positions includes:
determining a horizontal image distance between the monocular pupil and the marker according to the pupil image position of the monocular pupil and the mark position; and
determining the actual distance between the pupils of two eyes according to the horizontal image distance between the monocular pupil and the marker.

7. The interpupillary distance measuring method according to claim 6, wherein determining the actual distance between the pupils of two eyes according to the horizontal image distance between the monocular pupil and the marker includes:
measuring a vertical actual distance between the two eyes and a camera;
determining a FOV of the camera;
reading the horizontal image distance between the monocular pupil and the marker;
reading a height of the eye image; and
determining the actual distance between the pupils of two eyes according to the vertical actual distance between the two eyes and the camera, the FOV, the horizontal image distance between the monocular pupil and the marker, and the height of the eye image.

8. A wearable ophthalmic device, comprising: a processor and a memory, wherein
the memory stores instructions, and the following operations are implemented when the instructions are executed by the processor:
extracting one pupil image position corresponding to a monocular pupil from one eye image including one eye or extracting two pupil image positions corresponding to pupils of two eyes from two eye images each of which includes one eye; and
determining an actual distance between the pupils of two eyes according to the one or two pupil image positions, wherein the wearable ophthalmic device further comprises a first camera, and the first camera is configured to capture an eye image including the pupils of two eyes; and
the following operations are implemented when the instructions stored in the memory are executed by the processor:
determining the pupil image positions of the pupils of two eyes in the eye image;
determining an image distance of the pupils of two eyes on the eye image according to the pupil image positions of the pupils of two eyes; and
determining the actual distance between the pupils of two eyes according to the image distance of the pupils of two eyes.

9. The wearable ophthalmic device according to claim 8, further comprising an infrared source, wherein the infrared source provides a light source for the wearable ophthalmic device to capture an eye image.

* * * * *